United States Patent
Lo et al.

(10) Patent No.: US 9,259,167 B2
(45) Date of Patent: Feb. 16, 2016

(54) METHOD AND SYSTEM FOR EXTRACTING VENTRICULAR FIBRILLATION SIGNALS IN ELECTROCARDIOGRAM

(71) Applicant: National Central University, Jhongli, Taoyuan County (TW)

(72) Inventors: Men-Tzung Lo, Jhongli (TW); Wan-Hsin Hsieh, Jhongli (TW); Chen Lin, Jhongli (TW); Yi-Chung Chang, Jhongli (TW); Hsiang-Chih Chang, Jhongli (TW); Lian-Yu Lin, Taipei (TW); Patrick Chow-In Ko, Taipei (TW); Wen-Chu Chiang, Taichung (TW); Matthew Huei-Ming Ma, Taipei (TW); Kun Hu, Jhongli (TW)

(73) Assignee: NATIONAL CENTRAL UNIVERSITY, Jhongli, Taoyuan County (TW)

( * ) Notice: Subject to any disclaimer, the term of this patent is extended or adjusted under 35 U.S.C. 154(b) by 0 days.

(21) Appl. No.: 14/322,497

(22) Filed: Jul. 2, 2014

(65) Prior Publication Data
US 2016/0000346 A1  Jan. 7, 2016

(51) Int. Cl.
*A61B 5/04* (2006.01)
*A61B 5/046* (2006.01)
*A61B 5/00* (2006.01)

(52) U.S. Cl.
CPC ............. *A61B 5/046* (2013.01); *A61B 5/04012* (2013.01); *A61B 5/7207* (2013.01)

(58) Field of Classification Search
CPC .... A61B 5/04012; A61B 5/046; A61B 5/053; A61B 5/721; A61B 5/7282; A61B 5/7207; A61N 1/39
See application file for complete search history.

(56) References Cited

U.S. PATENT DOCUMENTS

2014/0100466 A1* 4/2014 Hayashi et al. ............... 600/509

OTHER PUBLICATIONS

Lo, Men-Tzung et al., A new method to estimate the amplitude spectrum analysis of ventricular fibrillation during cardiopulmonary resuscitation, Resuscitation, 2013, vol. 84, pp. 1505-1511.

* cited by examiner

*Primary Examiner* — George Manuel
(74) *Attorney, Agent, or Firm* — Muncy, Geissler, Olds & Lowe, P.C.

(57) ABSTRACT

This invention discloses a system and method for extracting VF signal in ECG recorded during uninterrupted CPR. The method and system applies an adaptive algorithm incorporating the EMD and least mean square (LMS) filtering to effectively model the CPR artifacts such as chest compression signals. Thus, A VF signal in ECG recorded during uninterrupted CPR can be extracted without deteriorating the reliability of the waveform parameter (i.e. AMSA) of shockability. The present invention enables uninterrupted CPR performed during recording ECG for accessing the shockability, so that an increase the probability of successful resuscitation is achieved.

18 Claims, 7 Drawing Sheets

1 second

METHOD AND SYSTEM FOR EXTRACTING VENTRICULAR FIBRILLATION SIGNALS IN ELECTROCARDIOGRAM

FIELD OF THE INVENTION

The invention relates to a method and system for extracting ventricular fibrillation (VF) signals, more particularly, to a method and system for extracting ventricular fibrillation (VF) signals in electrocardiogram (ECG) recorded during uninterrupted Cardio Pulmonary Resuscitation (CPR).

BACKGROUND OF THE INVENTION

Ventricular fibrillation (VF) is the most common etiology leading to sudden cardiac death. Early defibrillation and non-interrupted Cardio Pulmonary Resuscitation (CPR) are the most important determinants for restoration of spontaneous circulation in patients with VF. The occurrence of VF out of hospital makes early defibrillation hard to be realized. Fortunately, the VF waveform analysis such as amplitude spectrum analysis (AMSA) could help estimate the duration of VF, determine the shockability by assessing the VF waveform as being fine or coarse, and predict the probability of successful defibrillation, and has been applied to the conventional Automatic External Defibrillator (AED) for providing early defibrillation during the occurrence of VF out of hospital.

Although studies have demonstrated interruption of CPR greatly decreases the probability of successful resuscitation, non-interrupted CPR during recording Electrocardiography (ECG) for the VF waveform analysis is still a challenge. As shown in FIG. 1, chest compression related signals appearing in ECG which are caused from the CPR are often nonstationary and nonlinear rendering the linear-based analytic methods such as Fourier or wavelet-based analysis ineffective. Even though AMSA was claimed to be estimated with no interruption of CPR, CPR artifacts such as chest compression related signals are supposed to deteriorate the reliability and accuracy of VF waveform analysis because of power leak in spectrum analysis. As a result, it is usually required to discontinue CPR during recording ECG for the current VF waveform analysis to avoid the chest compression related signals mixing in ECG.

There are many solutions to the above challenge. The conventional filtering methods such as fixed coefficient high-pass filtering and adaptive band-stop filtering are still not desirable. Therefore, persons of ordinary skill in the art are imperative to develop a new analysis method which can be applied on the ECG recorded during uninterrupted CPR to not only reconstruct the morphology of VF waveforms but also to preserve the waveform parameter (i.e. AMSA) of shockability.

SUMMARY OF THE INVENTION

The present invention discloses a method and system for extracting a VF signal in ECG. The method and system applies an adaptive algorithm incorporating the EMD and least mean square (LMS) filtering to effectively model the CPR artifacts such as chest compression related signals commonly with time-varying amplitudes and compression rates. A VF signal in ECG recorded during uninterrupted CPR can be extracted without deteriorating the reliability of the waveform parameter (i.e. AMSA) of shockability. That is to say, the present invention enables uninterrupted CPR performed during recording ECG for accessing the shockability.

The present invention provides a method for extracting a Ventricular Fibrillation (VF) signal in Electrocardiography (ECG), comprising: receiving an ECG signal; decomposing the ECG signal by using an Empirical Mode Decomposition (EMD) method to generate a plurality of Intrinsic Mode Functions (IMFs); combining some IMFs with the same property to obtain a shape function which is similar as the variation of chest compression; correcting errors for each cycle of the shape function to obtain a compression signal; and subtracting the compression signal from the ECG signal to obtain the VF signal.

The present invention also provides a system for extracting a VF signal in ECG, comprising: a signal collecting unit configured to receive an ECG signal; a signal processing unit electrically connected to the signal collecting unit, the signal processing unit decomposing the ECG signal by using an EMD method to generate a plurality of IMFs, combining some IMFs with the same property to obtain a shape function which is similar as the variation of chest compression, correcting errors for each cycle of the shape function to obtain a compression signal, and subtracting the compression signal from the ECG signal to obtain the VF signal; and a signal outputting unit connected to the signal processing unit to outputting the VF signal.

The present invention further provides a method for extracting a VF signal in ECG, comprising: receiving an ECG signal; receiving a reference signal; modeling the reference signal with a LMS-refined shape function to obtain a compression signal; and subtracting the compression signal from the ECG signal to obtain the VF signal; and wherein the LMS-refined shape function expresses as provided by (S1)

$$\hat{S}_{CPR}(t) = \sum_{k=1}^{K} A_k(n)\cos(2\pi k f_0(n)t/f_s + \theta_k(t)) \qquad (S1)$$

$$= \sum_{k=1}^{K} a_k(n, t)\cos(2\pi k f_0(n)t/f_s) + b_k(n, t)\sin(2\pi k f_0(n)t/f_s)$$

$$= \sum_{k=1}^{K} a_k(n, t)\cos(k\phi(n, t)) + b_k(n, t)\sin(k\phi(n, t))$$

where $\hat{S}_{CPR}(t)$ is the compression signal, $f_0(n)$ is the time-varying frequency of n-th compression, $f_s$ is the sampling rate, $\theta_k(t)$ denotes the time-varying phase corresponding to k-th harmonic signal, $\phi(n,t)=2\pi f_0(n)t/f_s$, and $a_k(n,t)$ and $b_k(n, t)$ are the time-varying in-phase and quadrature coefficients of the filter for n-th compression.

The detailed features and advantages of the present invention will be described in detail with reference to the preferred embodiment so as to enable persons skilled in the art to gain insight into the technical disclosure of the present invention, implement the present invention accordingly, and readily understand the objectives and advantages of the present invention by perusal of the contents disclosed in the specification, the claims, and the accompanying drawings.

DETAILED DESCRIPTION OF THE INVENTION

Figure 2:
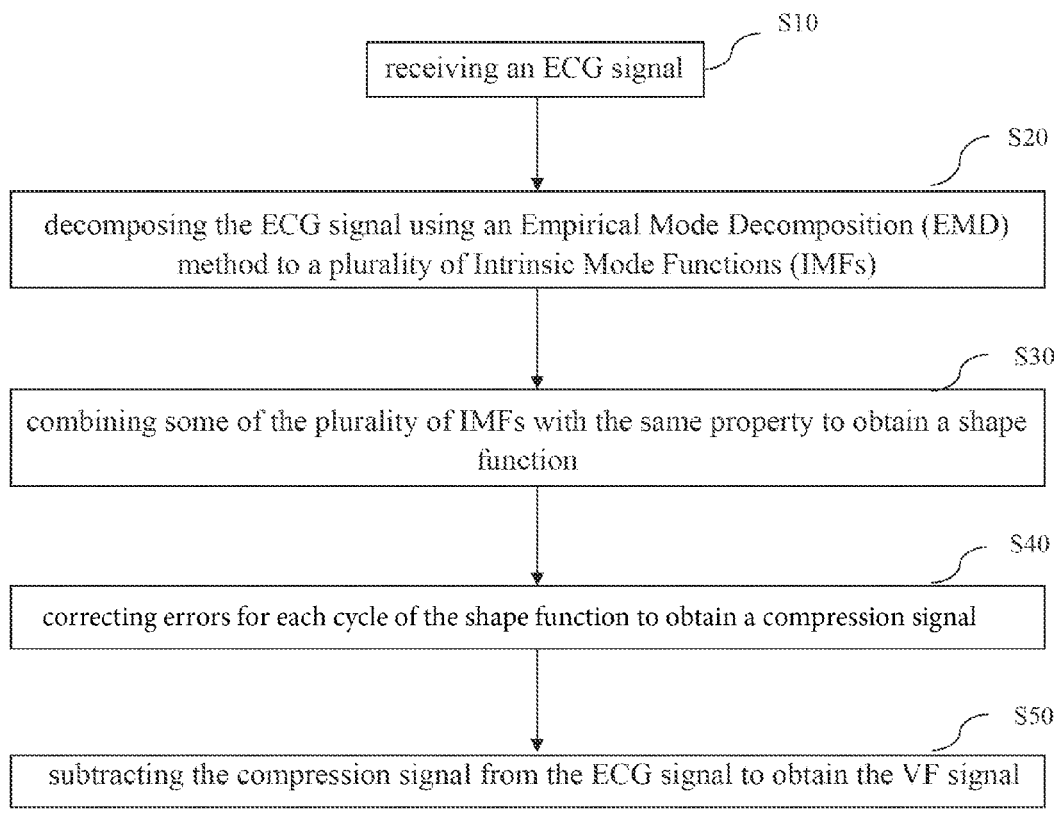
FIG. 2 shows a block diagram according to one exemplary embodiment.
Figure 3:
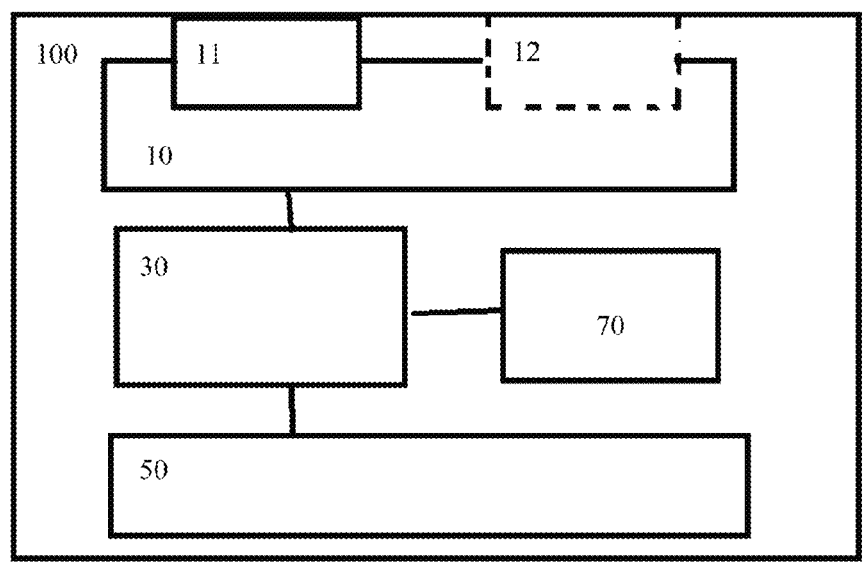
FIG. 3 is a flow chart according to one exemplary embodiment.

FIG. 2 and FIG. 3 respectively show a system 100 and a method S100 for extracting a VF signal in ECG according to an embodiment of the present invention. The method S100 may be implemented in the system 100. The system 100 includes a signal collecting unit 10, a signal processing unit 30, and a signal outputting unit 50. The signal collecting unit 10 is electrically connected to the signal processing unit 30. Meanwhile, the signal processing unit 30 is electrically connected to the signal outputting unit 50.

The method S100 and the system 100 can be applied on a mobile phone, an AED, a notebook, or a computer, which is not limited herein. The method S100 for extracting a VF signal in ECG includes the steps of: receiving an ECG signal (step S10); decomposing the ECG signal by using an Empirical Mode Decomposition (EMD) method to generate a plurality of Intrinsic Mode Functions (IMFs) (step S20); combining some IMFs with the same property to obtain a shape function (step S30); identifying each cycle (the cycle can be defining, such as a cycle of each chest compression action, will not be limitation) and correcting errors for each cycle of the shape function to obtain a compression signal (step S40). In an example, it may uses the Least Mean Square (LMS) method to obtain the compression signal; and subtracting the compression signal from the ECG signal to obtain the VF signal (step S50).

Firstly, the signal collecting unit 10 receives an ECG signal (step S10) through an ECG port 11. In another embodiment, the signal collecting unit 10 may receive the ECG signal wirelessly. The ECG signal may be recorded from a patient with VF or suspected VF without stopping the CPR procedure, so that the recorded ECG signal carries some chest compression related signals which may affect the following VF waveform analysis for determining the shockability.

Figure 1:
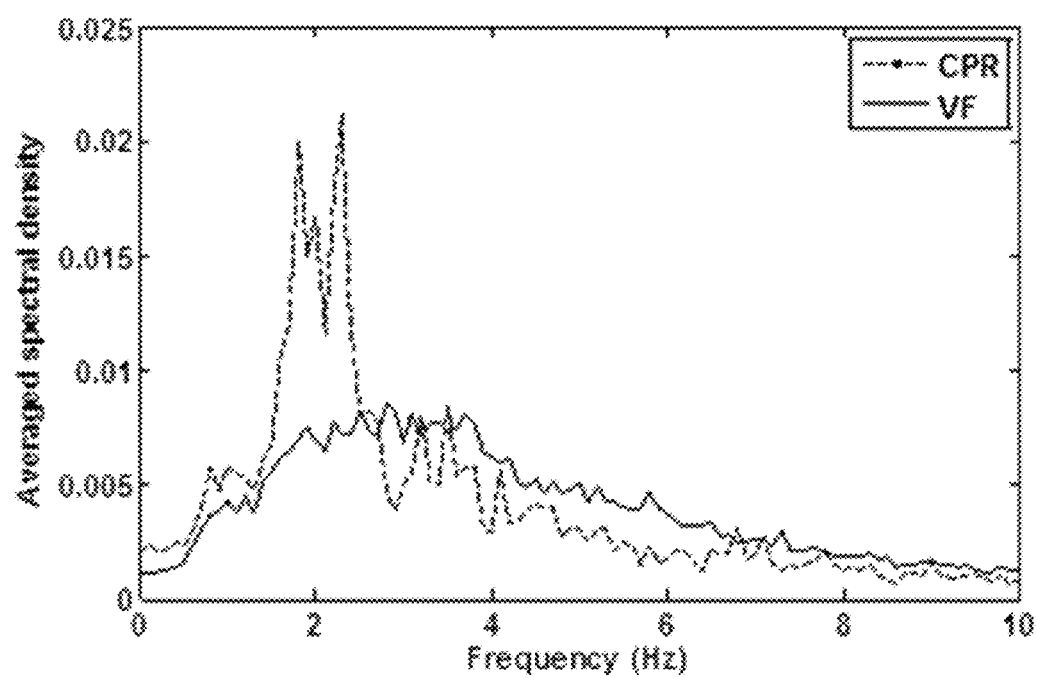
FIG. 1 shows a comparison of a CPR signal and a VF signal in a chest compression action.

The compression signals, such as chest compression related signals, are characterized as broadband and nonlinear. Besides, the frequency bands of the compression signals and the VF signal overlap with each other (see FIG. 1). Empirical Mode Decomposition (EMD) developed by Norden Huang's group in National Aeronautics and Space Administration (NASA) is designed to extract nonlinear, dynamic information from nonstationary signals at different time scales and has the advantages of being able to handle short, nonstationary, and nonlinear datasets.

The method of EMD, or Ensemble Empirical Mode Decomposition (EEMD) which further considers adding a white noise to the original signal, can decompose a time sequence signal to a plurality of intrinsic mode functions, and the shifting processes are as follows: (1) All limit values are identified in the time sequence signal, and all maximum values are connected with each other to form as an upper envelope, and all minimum values are connected with each other to form as a lower envelope via a cubic spline. (2) A data is subtracted from an average envelope of the upper envelope and the lower envelope to obtain a first measure of weight. (3) The steps (1) and the step (2) are executed repeatedly until the upper and lower envelope symmetrizing with an axis of time.

In sum, the method of EMD is a self-adaptive modal decomposition method. A time sequence signal is decomposed to a finite number of intrinsic mode functions in accordance with the dynamic time sequence signal from high disturbance frequency to low disturbance frequency gradually.

Figure 4A:
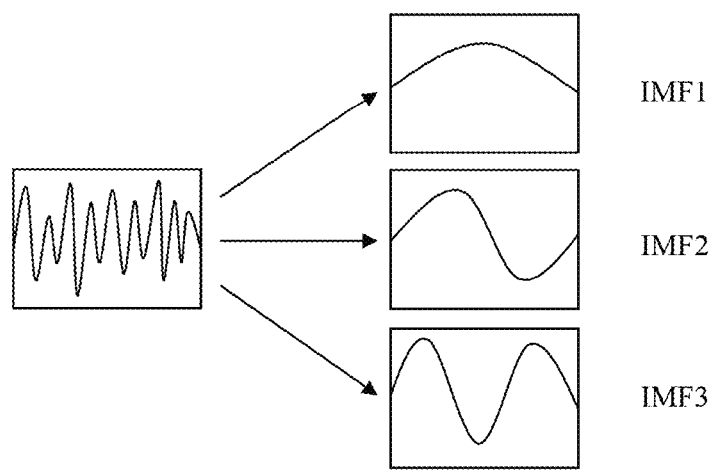
FIG. 4a illustrates decomposing the ECG signal to a plurality of IMFs.

Please refer to FIG. 4a, the signal processing unit 30 decomposes the ECG signal using an Empirical Mode Decomposition (EMD) method (or an Ensemble Empirical Mode Decomposition (EEMD)) to a plurality of Intrinsic Mode Functions (IMFs) (step S20) with different equivalent (frequency) and a plurality of local means. Each of the plurality of IMFs is an expression of one equivalent in the received signal, and each equivalent corresponds to one of the IMFs.

An EMD(EEMD) can decompose a nonlinear and non-stationary time series into its intrinsic mode functions (IMFs). Each IMF represents a frequency-amplitude modulation in a narrow band that can be related to a specific physical or physiologic process. Given a signal x(t), the procedure of the EMD starts identifying all the local maxima and minima. All the local maxima are then connected by a cubic spline curve as the upper envelope $e_u(t)$. Similarly, all the local minima are connected by a spline curve as the lower envelope $e_l(t)$. The mean of the two envelopes is denoted as $m^{(1)}(t)=(e_u(t)+e_l(t))/2$, and it is subtracted from x(t) to obtain the first component $h^{(1)}(t)=x(t)-m^{(1)}(t)$. The above procedure is referred to as the sifting process. Since $h^1(t)$ still contains multiple extrema between zero crossings, the sifting process is performed again on $h^{(1)}(t)$. This process is applied repetitively to the component $h^{(k)}(t)$ to get satisfactory IMF. We can separate $c_1(t)$ from the data by $r_1(t)=x(t)-c_1(t)$.

Since the residue, $r_1(t)$, still contains information of longer period components, it is treated as new data and subjected to the same sifting process. This procedure can be repeated on all the subsequent residues, and the result is $$x(t)=c_1(t)+r_1(t)$$

$$=c_1(t)+c_2(t)+r_2(t)$$

$$\cdot$$
$$\cdot$$
$$\cdot$$

$$=c_1(t)+c_2(t)+\ldots+c_n(t) \qquad (S0)$$

Where $c_k(t)$ is the k-th IMF component and $r_k(t)$ is the residual after extracting the first k IMF components $$\left\{\text{i.e. } r_k(t) = x(t) - \sum_{i=1}^{k} c_i(t)\right\}.$$

The above procedure is repeated to obtain different IMFs at different scales until there are less than 2 minima or maxima in a residual which will be assigned as the last IMF.

Figure 4B:
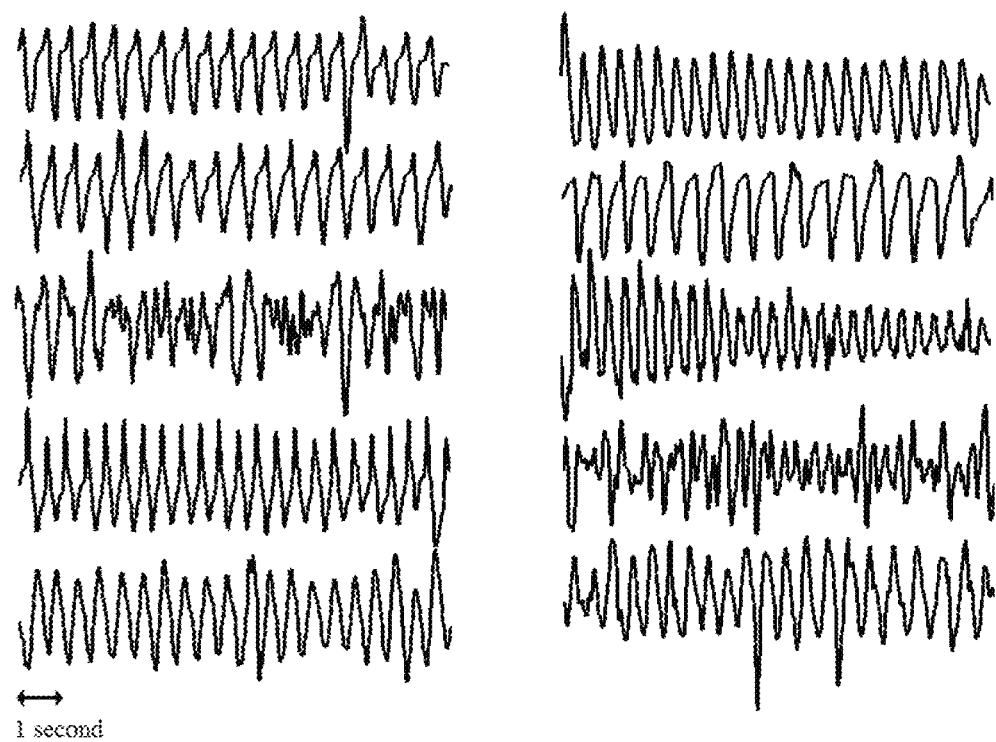
FIG. 4b demonstrates a plurality of IMFs in an ECG signal according to one exemplary embodiment.
Figure 5:
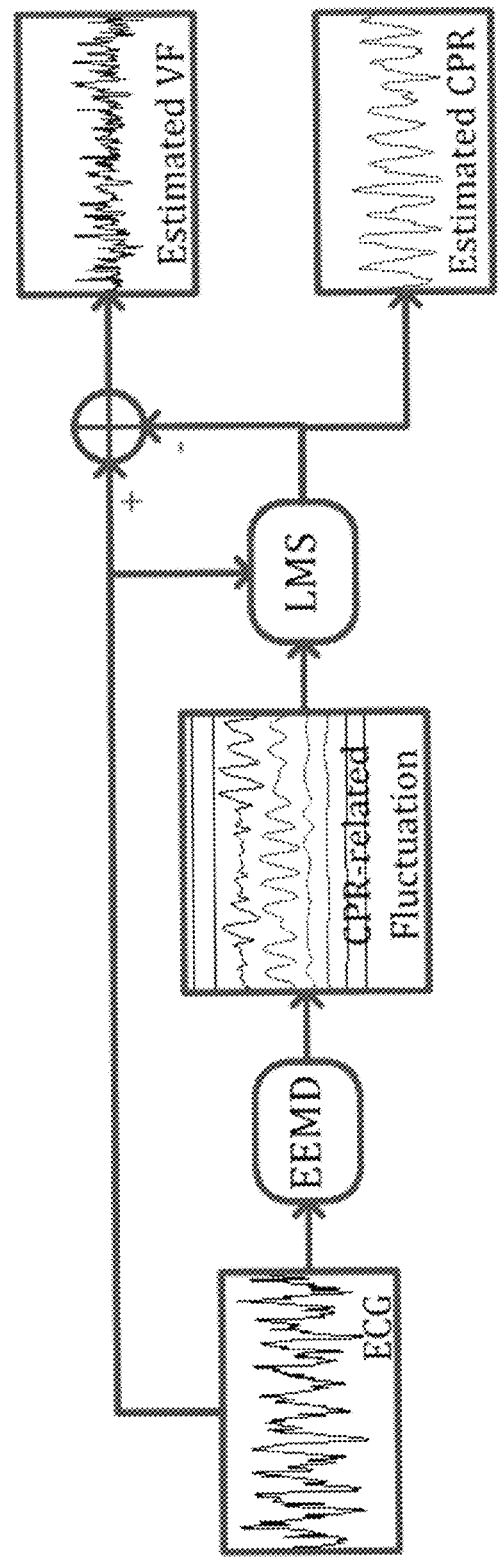
FIG. 5 shows one flow diagram according to one exemplary embodiment.

In one embodiment, the received signal may be the ECG signal, and is decomposed to a plurality of IMFs in FIG. 4b. Preferably, the ECG signal may be a function of amplitude and time. As shown in FIG. 5, the ECG signal is processed with EMD/EEMD to obtain the shape function for modeling the compression signal.

In another embodiment, as shown in FIG. 2, the signal collecting unit 10 may include an ECG port 11 and a reference signal port 12 The signal collecting unit 10 may receive a reference signal which is related with the chest compressions variation of CPR through the reference signal port 12 while receiving the ECG signal. An inexpensive accelerometer such as a wrist accelerometer measures the reference signal according to the acceleration generated from the chest compression movement during CPR. Preferably, the reference signal may be a function of amplitude and time.

Figure 6:
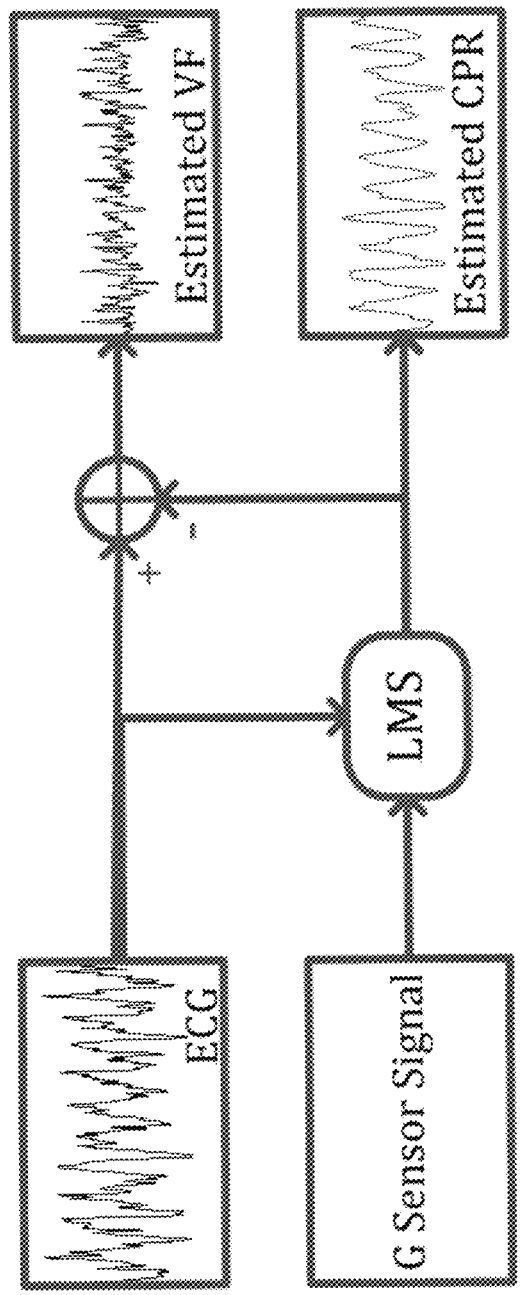
FIG. 6 shows another flow diagram according to one exemplary embodiment.

As shown in FIG. 6, the reference signal may be processed with EMD/EEMD to obtain the shape function for modeling the compression signal. In another embodiment, the process may be simplified to model the reference signal with a LMS-refined shape function to obtain the compression signal without processing the EMD in advance. The LMS-refined shape function may be derived with the following description, and may be stored in a storage unit 70 of the system 100 in advance. The storage unit 70 may be electrically connected to the signal processing unit 30.

The reference signal may be applied to more accurately estimate the compression signal than the ECG signal does because it is more directly related with the chest compression movement during CPR. If the signal collecting unit 10 receives the reference signal, the received signal must be the reference signal. In one embodiment, the reference signal may be received wirelessly through RF protocol such as BlueRobin™.

Figure 7:
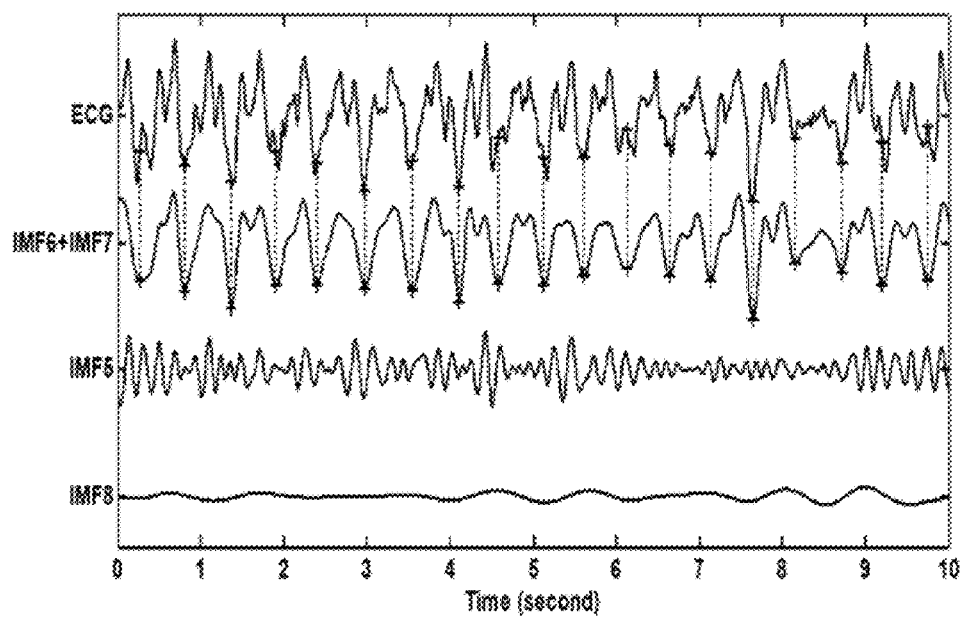
FIG. 7 demonstrates the reconstructed ECG signal, the combined IMFs and other remaining IMFs according to one exemplary embodiment.

Referring to FIG. 7, in one preferred embodiment, the signal processing unit 30 preferably removes some IMFs with a frequency higher than the chest compression frequency and combines the remaining IMFs to reconstruct the ECG signal.

The signal processing unit 30 combines some of the plurality of IMFs with the same property to obtain a shape function (step S30). In this step, some IMFs features the compression signal should be chosen.

Generally speaking, the signal strength of the compression signal is prominently larger than that of the VF signal. That's why we considered the main fluctuations of ECG signal are from the compression signal. Some IMFs featuring the compression signal may have the same property with the ECG signal. As a result, calculates the correlation coefficient of each IMF and the ECG signal, and then selecting some of IMFs with higher correlation coefficient than others (see IMF6 and IMF7 in FIG. 7). Combining the IMFs may obtain a shape function which almost reconstructs the fluctuation of the compression signal.

The time interval for each chest compression can be easily identified (see "+" symbol in the chest compression-related fluctuation of FIG. 5) and correctly estimated from the shape function reconstructed by EMD/EEMD. The rate of each compression was then determined by the inverse of the compression cycle lengths.

After identifying the rates of chest compressions, the signal processing unit 30 models the shape function using the Least Mean Square (LMS) to obtain a compression signal (step S40). The shape function is further refined through step S40. The LMS model hypothesizes that each chest compression signal (each cycle of shape function) is composed of K harmonics of the sinusoids with variable period determined by the EMD derived the shape function. Therefore, the chest compression signal with time varying compression rates was further elaborated by LMS model as provided by $$\hat{S}_{CPR}(t) = \sum_{k=1}^{K} A_k(n)\cos(2\pi k f_0(n)t/f_s + \theta_k(t)) \quad (S1)$$

$$= \sum_{k=1}^{K} a_k(n,t)\cos(2\pi k f_0(n)t/f_s) + b_k(n,t)\sin(2\pi k f_0(n)t/f_s)$$

$$= \sum_{k=1}^{K} a_k(n,t)\cos(k\phi(n,t)) + b_k(n,t)\sin(k\phi(n,t))$$

where $f_0(n)$ was the time-varying frequency of n-th compression, $f_s$ was the sampling rate, $\theta_k(t)$ denoted the time-varying phase corresponding to k-th harmonic signal, $\phi(n,t)=2\pi f_0(n) t/f_s$ and $a_k(n,t)$ and $b_k(n,t)$ were the time-varying in-phase and quadrature coefficients of the filter for n-th compression. S1 may be the LMS-refined shape function, and may be stored in the storage unit 70 in advance for the simplified process.

Note that the time-varying frequency $f_0(n)$ was obtained by the inverse of cycle length of n-th compression in the shape function. For modeling compressions cycle by cycle, Equation (S1) could be simplified by $$\hat{S}_{CPR}(t) = \sum_{k=1}^{K} a_k(t)\cos(k\phi(t)) + b_k(t)\sin(k\phi(t)). \quad (S2)$$

In each compression cycle, $a_k(t)$ and $b_k(t)$ would be trained and repeatedly updated according to the difference between ECG signal and modeled shape function in LMS algorithm. Let a(t) and b(t) be the column vectors of the in-phase and the quadrature filter coefficients at time k in two column vectors, namely $$a(t)=[a_1(t),\ldots,a_K(t)]^T \quad (S3)$$

$$b(t)=[b_1(t),\ldots,b_K(t)]^T. \quad (S4)$$

Furthermore, let K in-phase and quadrature harmonics signals be expressed by the row vectors $$I(t)=[\cos(\phi(t)),\ldots,\cos(K\phi(t))] \quad (S5)$$

$$Q(t)=[\sin(\phi(t)),\ldots,\sin(K\phi(t))]. \quad (S6)$$

Assume the ECG signal is S(t), the difference between ECG signal and modeled shape function was provided by $$e(t)=S(t)-\hat{S}_{CPR}(t). \quad (S7)$$

We denote the matrix regarding the step size for updating the coefficient in each harmonic component as $$U = \begin{bmatrix} \mu_1 & \cdots & 0 \\ 0 & \ddots & 0 \\ 0 & \cdots & \mu_K \end{bmatrix} = \begin{bmatrix} \mu_0 & \cdots & 0 \\ 0 & \ddots & 0 \\ 0 & \cdots & \mu_0/K \end{bmatrix} \quad (S8)$$

where $\mu_0=0.007$.

The training equations of the filter coefficient in LMS algorithm for each chest compression cycle were provided by $$a(t+1)=a(t)+2e(t)UI^T(t) \quad (S9)$$

$$b(t+1)=b(t)+2e(t)UQ^T(t). \quad (S10)$$

where the initial value of the coefficients, i.e. a(0) and b(0), were all zero.

Figure 8:
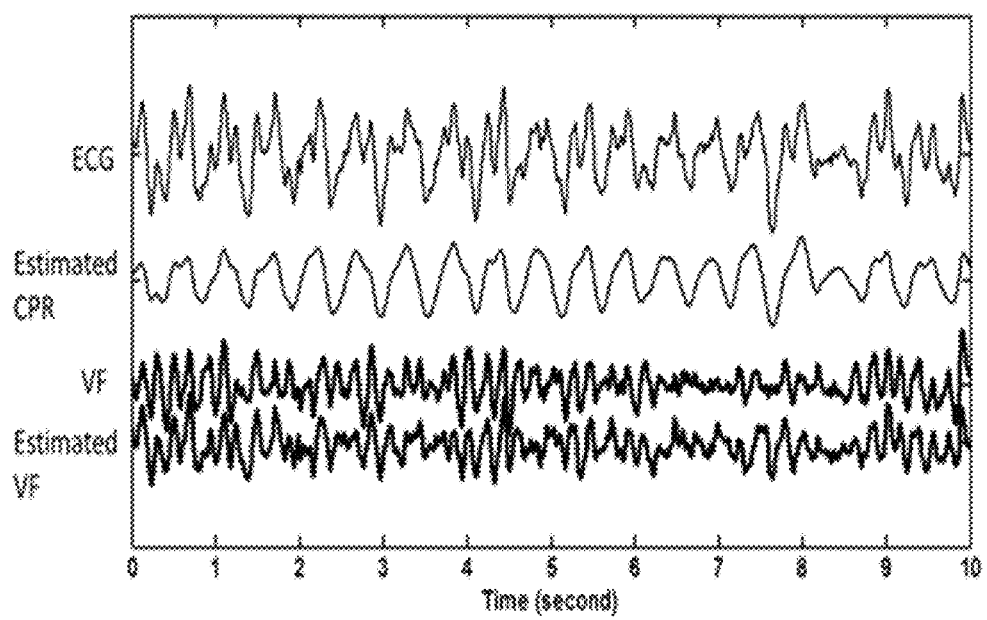
FIG. 8 shows a comparison of the ECG signal, the compression signal, the actual VF signal and the VF signal estimated in one exemplary embodiment.

In our LMS model, we consider five harmonic components, i.e. $K=5$ in Eq. (S2). In addition, when $f_0(n)>10$ Hz, we set K=1 in the model because other higher harmonics would be significantly influenced by the VF components. After training the coefficients for a compression cycle, the coefficients were converged and were used for model the associated compression signal. However, because the shape function was modeled cycle by cycle, discontinuity between consecutive compression cycles might occur. Here, the discontinuity was remedied by the average of upper and lower spline constructed by adjacent points near the discontinuity. After the shape function was modeled by LMS algorithm in cycle-wise manner to obtain a compression signal, the VF signal was obtained by subtracting the compression signal from the ECG signal (step S50) in the signal processing unit 50. The VF signal estimated in this embodiment is shown in FIG. 8, which resembled the actual VF signal. Finally, the signal outputting unit 50 may be configured to output the VF signal, which is not limited herein.

The accurately extracted VF signal may be applied to the VF waveform analysis to determine the shockability. Due to the high reliability of the proposed method and system, the waveform parameter (i.e. AMSA) of shockability determined by the extracted VF signal is reliable even the ECG signal is recorded during uninterrupted CPR. The present invention enables an increase in the probability of successful resuscitation.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

What is claimed is:

1. A method for extracting a Ventricular Fibrillation (VF) signal in Electrocardiography (ECG), comprising:
    receiving an ECG signal;
    decomposing the ECG signal by using an Empirical Mode Decomposition (EMD) method to generate a plurality of Intrinsic Mode Functions (IMFs);
    combining some IMFs with the same property to obtain a shape function;
    correcting errors for each cycle of the shape function to obtain a compression signal; and
    subtracting the compression signal from the ECG signal to obtain the VF signal.

2. The method according to claim 1, wherein the received signal is the ECG signal.

3. The method according to claim 1, wherein the ECG signal is a function of amplitude and time.

4. The method according to claim 1, further comprising: receiving a reference signal, wherein the received signal is the reference signal.

5. The method according to claim 4, wherein the reference signal is recorded by a wrist accelerometer.

6. The method according to claim 4, wherein the reference signal is a function of amplitude and time.

7. The method according to claim 1, wherein each of the IMFs is an expression of one equivalent in the received signal.

8. The method according to claim 1, wherein the IMFs with the same property are the IMFs having the higher correlation coefficient with the ECG signal.

9. The method according to claim 1, wherein the compression signal ($S_{CPR}$) elaborated by Least Mean Square (LMS) expresses as provided by (S1)

$$\hat{S}_{CPR}(t) = \sum_{k=1}^{K} A_k(n)\cos(2\pi k f_0(n)t/f_s + \theta_k(t)) \quad (S1)$$

$$= \sum_{k=1}^{K} a_k(n,t)\cos(2\pi k f_0(n)t/f_s) + b_k(n,t)\sin(2\pi k f_0(n)t/f_s)$$

$$= \sum_{k=1}^{K} a_k(n,t)\cos(k\phi(n,t)) + b_k(n,t)\sin(k\phi(n,t))$$

where $f_0(n)$ is the time-varying frequency of n-th compression, $f_s$ is the sampling rate, $\theta_k(t)$ denotes the time-varying phase corresponding to k-th harmonic signal, $\phi(n,t) = 2\pi f_0(n)t/f_s$ and $a_k(n,t)$ and $b_k(n,t)$ are the time-varying in-phase and quadrature coefficients of the filter for n-th compression.

10. A system for extracting a VF signal in ECG, comprising:
    a signal collecting unit, configured to receive an ECG signal;
    a signal processing unit, electrically connected to the signal collecting unit, the signal processing unit decomposing the ECG signal by using an EMD method to generate a plurality of IMFs, combining some IMFs with the same property to obtain a shape function, correcting errors for each cycle of the shape function to obtain a compression signal, and subtracting the compression signal from the ECG signal to obtain the VF signal; and
    a signal outputting unit, connected to the signal processing unit to output the VF signal.

11. The system according to claim 10, wherein the received signal is the ECG signal.

12. The system according to claim 10, wherein the ECG signal is a function of amplitude and time.

13. The system according to claim 10, wherein the signal collecting unit includes an ECG port to receive the ECG signal and a reference signal port to receive a reference signal, wherein the received signal is the reference signal.

14. The system according to claim 13, wherein the reference signal is recorded by a wrist accelerometer.

15. The system according to claim 13, wherein the reference signal is a function of amplitude and time.

16. The system according to claim 10, wherein each of the IMFs is an expression of one equivalent in the received signal.

17. The system according to claim 10, wherein the IMFs with the same property are the IMFs having the higher correlation coefficient with the ECG signal.

18. The system according to claim 10, wherein the compression signal ($S_{CPR}$) elaborated by Least Mean Square (LMS) expresses as provided by (S1)

$$\hat{S}_{CPR}(t) = \sum_{k=1}^{K} A_k(n)\cos(2\pi k f_0(n)t/f_s + \theta_k(t)) \quad (S1)$$

$$= \sum_{k=1}^{K} a_k(n,t)\cos(2\pi k f_0(n)t/f_s) + b_k(n,t)\sin(2\pi k f_0(n)t/f_s)$$

$$= \sum_{k=1}^{K} a_k(n,t)\cos(k\phi(n,t)) + b_k(n,t)\sin(k\phi(n,t))$$

where $f_0(n)$ is the time-varying frequency of n-th compression, $f_s$ is the sampling rate, $\theta_k(t)$ denotes the time-varying phase corresponding to k-th harmonic signal, $\phi(n,t) = 2\pi f_0(n)t/f_s$, and $a_k(n,t)$ and $b_k(n,t)$ are the time-varying in-phase and quadrature coefficients of the filter for n-th compression.

* * * * *